US006342515B1

(12) United States Patent
Masuda et al.

(10) Patent No.: US 6,342,515 B1
(45) Date of Patent: Jan. 29, 2002

(54) REMEDY FOR NEURODEGENERATIVE DISEASES

(75) Inventors: Yoshinobu Masuda, Katano; Yoshiaki Ochi, Sanda, both of (JP)

(73) Assignee: Dainippon Pharmaceutical Co., Ltd., Osaka-fu (JP)

( * ) Notice: Subject to any disclaimer, the term of this patent is extended or adjusted under 35 U.S.C. 154(b) by 0 days.

(21) Appl. No.: 09/582,433

(22) PCT Filed: Dec. 21, 1998

(86) PCT No.: PCT/JP98/05757

§ 371 Date: Jun. 26, 2000

§ 102(e) Date: Jun. 26, 2000

(87) PCT Pub. No.: WO99/33465

PCT Pub. Date: Jul. 8, 1999

(30) Foreign Application Priority Data

Dec. 26, 1997 (JP) ............................................... 9-369313

(51) Int. Cl.$^7$ ............................................... A61K 3/142
(52) U.S. Cl. ........................ 514/379; 514/878; 514/879
(58) Field of Search ................. 514/379, 878, 514/879

(56) References Cited

U.S. PATENT DOCUMENTS 4,172,896 A    10/1979  Uno et al.
5,128,354 A  *  7/1992  Masuda et al. ............. 514/379
5,830,910 A  * 11/1998  Mattson ...................... 514/411

OTHER PUBLICATIONS

Schwarz et al, "Postischemic diazepam is neuroprotective in the gerbil hippocampus . . . " Brain Research, 647 (1994), pp. 153–160.*
Rataud et al, "Comparative study of voltage–sensitive sodium channel blockers . . . ", Neuroscience Letters, 172 (1994), pp. 19–23.*
Jones–Humble, et al., "The novel anticonvulsant lamotrigine prevents dopamine depletion . . . ", Life Sciences, vol. 54, pp. 245–252.*
Chemical Abstract 122:178174k, "Effects of carbamazepine and zonisamide on dopaminergic system . . . " (1994).*
Okada, "Effects of carbamazepine and zonisamide on dopaminergic system", Jpn. J. Psychopharmacol. 14, pp. 337–354 (1994).*
Okada, M., "Effects of carbamazepine and zonisamide on dopaminergic system in rat striatum and hippocamus" Jpn-.J.Psychopharmacol., 1994, vol. 14, pp. 337–354 & Chemical Abstracts, 1995, page 79, Abstract No. 178174k.

* cited by examiner

Primary Examiner—Frederick Krass
(74) Attorney, Agent, or Firm—Wenderoth, Lind & Ponack, L.L.P.

(57) ABSTRACT

The present invention provides a medicament for neurodegenerative diseases comprising zonisamide or an alkali metal salt thereof as an active ingredient. The present medicament can be used in the prevention and treatment of neurodegenerative diseases such as Parkinson's disease, Huntington's disease, choreic syndrome and dystonic syndrome in mammals (including human).

24 Claims, 2 Drawing Sheets

REMEDY FOR NEURODEGENERATIVE DISEASES

This appln. is a 371 of PCT/JP 98/05757, filed Dec. 21, 1998.

TECHNICAL FIELD

The present invention relates to a medicament for neurodegenerative diseases comprising zonisamide or an alkali metal salt thereof as the active ingredient.

BACKGROUND ART

Zonisamide [chemical name: 3-sulfamoylmethyl-1,2-benzisoxazole or 1,2-benzisoxazole-3-methanesulfonamide; see, for example, Merck Index, 12th Ed., 10323 (1996)] has been used as an antiepileptic agent in the treatment or prevention of various seizures in Japan, South Korea, etc. JP-B-60-33114, JP-B-61-59288 and U.S. Pat. No. 4,172,896 disclose processes for preparing zonisamide and the utility thereof as an antiepileptic agent. Further, JP-B-7-84384 and U.S. Pat. No. 5,128,354 also disclose the utility of zonisamide as a medicament for ischemic brain damage.

With developing into an aging society, the number of patients suffering from neurodegenerative diseases such as Parkinson's disease is increasing. Parkinson's disease is a progressive and tragic disease by which coordinated movement of patient is disturbed, and the movement of patient becomes slow with the lapse of time, and finally, rigidity or tremor of arms and legs develop. It has been known that said disease is caused by depletion of striatum dopamine due to rhexis and loss of dopamine-producing neurons in nigrostriatal.

Incidentally, a striatal dopamine-depleted animal, which is prepared by administering 1-methyl-4-phenyl-1,2,3,6-tetrahydropyridine (hereinafter, referred to as "MPTP") to a C57 black mouse, has been widely used as an animal model for Parkinson's disease. Life Sci., 54, 245 (1994) discloses that antiepileptic agents: lamotrigine [chemical name: 3,5-diamino-6-(2,3-dichlorophenyl)-1,2,4-triazine] and phenytoin show an inhibitory effect on dopamine depletion induced by MPTP, while carbamazepine does not show such effect. However, in the experiments of said literature, MPTP hydrochloride was subcutaneously injected at a dose of 15 mg/kg only once to C57 black mice, and therefore said mice are not necessarily suitable as an animal model for Parkinson's disease.

In the current medication of Parkinson's disease, there are used dopamine replenishing agents (e.g., levodopa alone, or a combination product or combined therapy of levodopa and carbidopa), dopaminergic agonists (e.g., bromocriptine or terguride), dopamine releasing agents (e.g., amantadine), anticholinergic agents (e.g., biperiden or trihexyphenidyl), monoamine oxidase type B (MAO-B) inhibitors (e.g., selegiline), etc. However, these agents are not necessarily satisfactory from the viewpoint of efficacy and side effects, and it has been expected to develop a novel effective medicament.

The present inventors have found that zonisamide and an alkali metal salt thereof exhibit an extremely potent inhibitory effect on the MPTP-induced dopaminergic neurodegeneration, and have accomplished the present invention.

DISCLOSURE OF INVENTION

An object of the present invention is to provide a medicament for the treatment of neurodegenerative diseases comprising zonisamide or an alkali metal salt thereof as an active ingredient.

Another object of the present invention is to provide use of zonisamide or an alkali metal salt thereof for the manufacture of a medicament for neurodegenerative diseases.

A further object of the present invention is to provide a method for the prevention and/or treatment of neurodegenerative diseases in a mammal (including human), which comprises administering an effective amount of zonisamide or an alkali metal salt thereof to said mammal in need of such prevention and/or treatment.

BEST MODE FOR CARRYING OUT THE INVENTION

Figure 1:
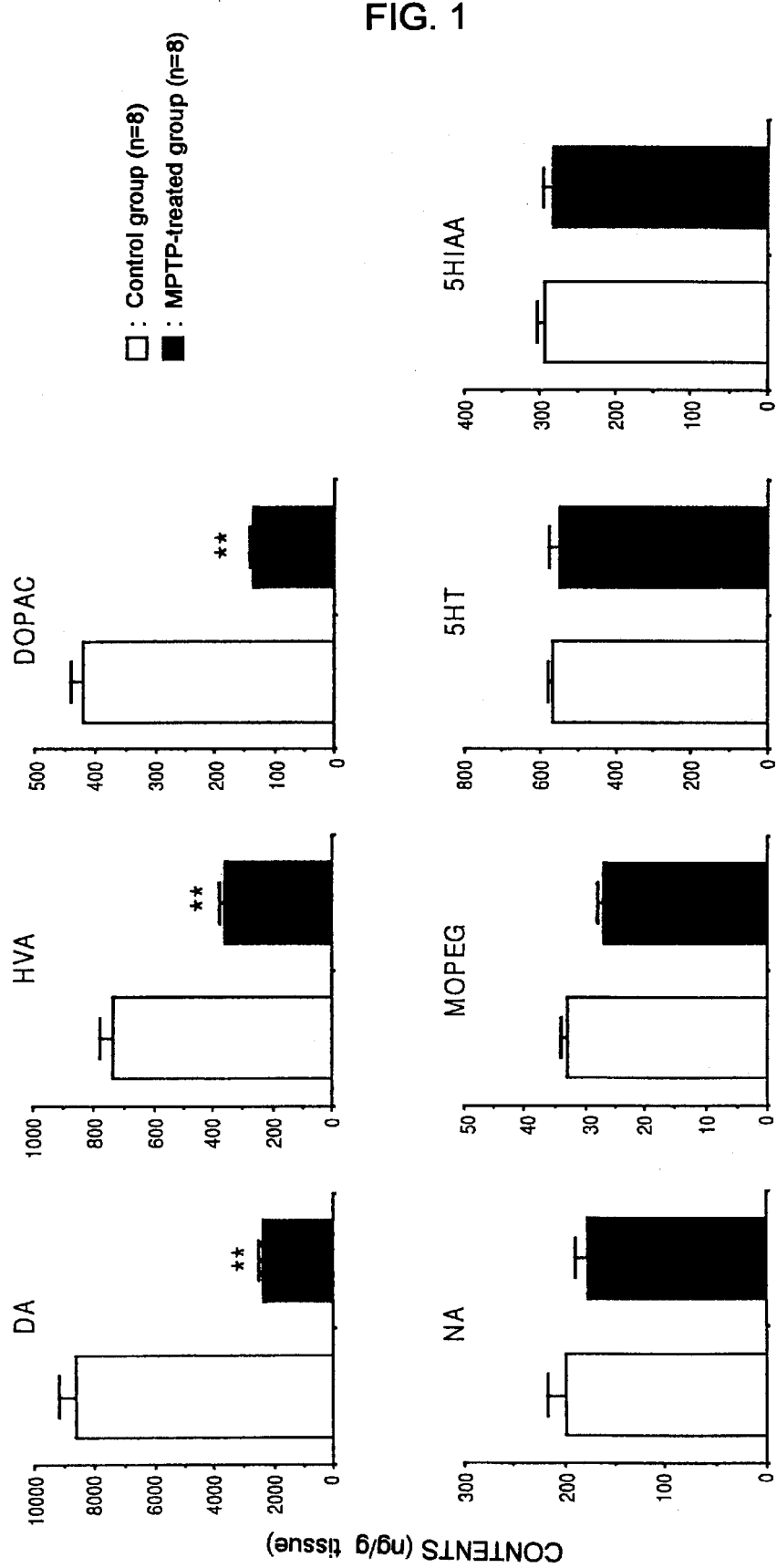
FIG. 1 is a graph showing the contents of various monoamine neurotransmitters and metabolites thereof in the striatum excised 24 hours after the last administration of MPTP from C57 black male mice, to which MPTP hydrochloride was administered intraperitoneally once a day at a dose of 30 mg/kg for 8 days repetitively.

Examples of alkali metal salts of zonisamide are sodium salt, potassium salt, and lithium salt. Zonisamide may be prepared, for example, by the methods disclosed in JP-B-60-33114, JP-B-61-59288 and U.S. Pat. No. 4,172,896.

The results of the pharmacological experiments of zonisamide and known antiepileptic agents are shown below, and thereby the utility of zonisamide as a medicament for neurodegenerative diseases will be explained. Antiepileptic agents used as reference drugs in the pharmacological experiments are listed below.

Carbamazepine (see, for example, Merck Index, 12th Ed., 1826 (1996));

Phenytoin (see, for example, Merck Index, 12th Ed., 7475 (1996));

Lamotrigine (see, for example, Merck Index, 12th Ed., 5367 (1996));

Phenobarbital (see, for example, Merck Index, 12th Ed., 7386 (1996));

Ethosuximide (see, for example, Merck Index, 12th Ed., 3794 (1996));

Sodium valproate (see, for example, Merck Index, 12th Ed., 10049 (1996));

Diazepam (see, for example, Merck Index, 12th Ed., 3042 (1996)); and

Acetazolamide (see, for example, Merck Index, 12th Ed., 50 (1996)).

In each experiment, the contents of monoamine neurotransmitters and metabolites thereof in the striatum were measured by high performance liquid chromatography (HPLC) method. HPLC was carried out using a system consisting of a pump (L-6000, manufactured by Hitachi, Ltd., Japan), an autoinjector, a column (Cosmosil 5C18-A, manufactured by Nacalai Tesque, Inc., Japan; 4.6Ø×250 mm), and an electrochemical detector (ECD-100, manufactured by Eicom Corporation, Japan) under the following conditions.

Mobile phase: 0.05 M Citric acid containing 0.075 M sodium perchlorate:acetonitrile buffer (92.5:7.5, pH 4.3)

Said buffer contained 0.022% sodium octasulfonate and 0.0015% EDTA·2 sodium salt.

Flow rate: 0.9 ml/min.

Conditions for Detection:

Work electrode: Graphite electrode

Reference electrode: Silver/Silver chloride

Applied voltage: 750 mV

In addition, the statistical analysis was carried out by Dunnett's multiple comparison test.

Experiment 1

Preparation of Animal Model for Parkinson's Disease:

C57 black male mice (11-week-old) were used in the experiment. MPTP hydrochloride was dissolved in a physiological saline solution in a concentration of 3 mg/ml, and the resulting solution was intraperitoneally injected to the mice in a volume of 0.1 ml per 10 g of body weight, i.e., at a dose of 30 mg/kg, once a day for 8 days repetitively. Twenty-four hours after the last MPTP administration, the head of the mouse was subjected to microwave irradiation, and the striatum was excised therefrom.

The striatum excised was homogenized with a 50-fold volume of 0.1 N formic acid:acetone (15:85) containing an internal standard substance (5-hydroxytriptophol; 20 ng/ml), and the mixture was centrifuged under cooling. A fixed amount of the supernatant was collected and evaporated to dryness under stream of nitrogen gas. Then, the resultant was dissolved in a 0.01 N acetic acid and centrifuged, and then the contents of various monoamine neurotransmitters and metabolites thereof in the supernatant were measured by HPLC being equipped with an electrochemical detector.

The changes in the contents of various neurotransmitters and metabolites thereof 24 hours after the last MPTP administration are shown in FIG. 1. The number of animals in each group is 8, and the perpendicular lines in the figures represent standard errors, and the mark ** means that there is a significant difference from the value of the control group (the group treated with a physiological saline solution) with $p<0.01$.

As is clear from FIG. 1, MPTP significantly reduced the contents of dopamine (DA) and metabolites thereof, homovanillic acid (HVA) and 3,4-dihydroxyphenylacetic acid (DOPAC), but never affected the contents of noradrenaline (NA), serotonin (5HT), and metabolites thereof, 3-methoxy-4-hydroxyphenylethyleneglycol (MOPEG) and 5-hydroxyindole-acetic acid (5HIAA), and thereby it was confirmed that MPTP exhibited the selectivity for dopaminergic neurons.

Figure 2:
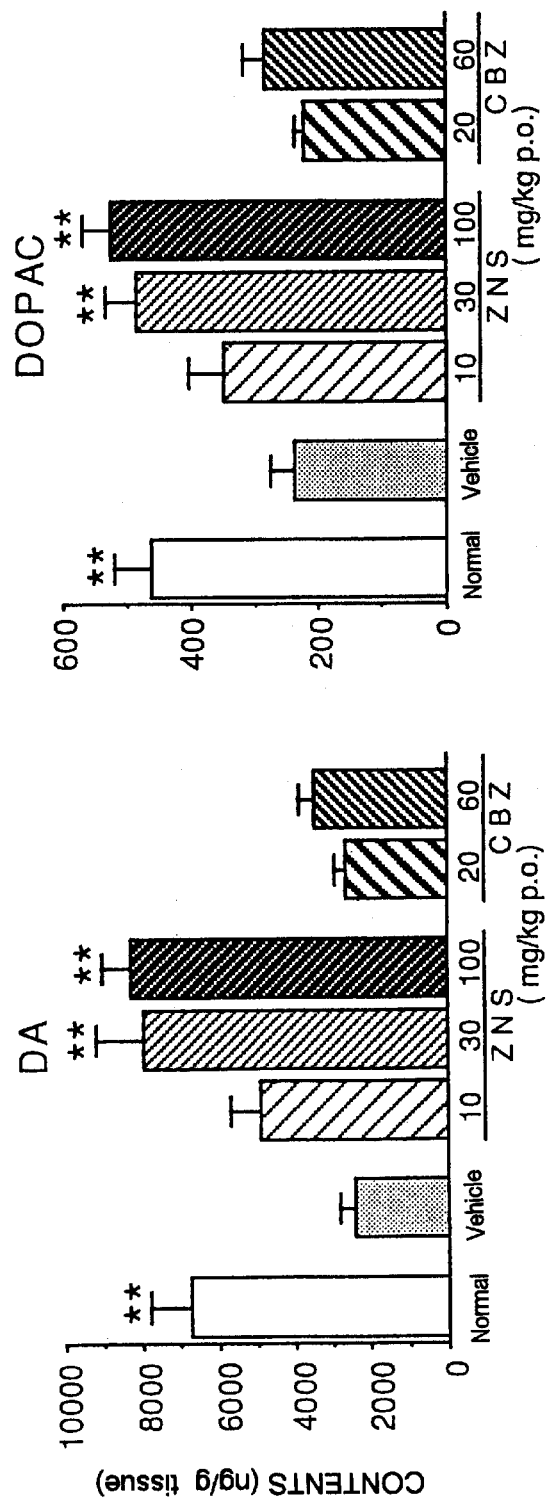
FIG. 2 is a graph showing the inhibitory effect of zonisamide and carbamazepine on the MPTP-induced dopaminergic neurodegeneration in C57 black male mice 14 days after the last administration of MPTP.

Further, since the reduction in the contents of dopamine and metabolites thereof in the striatum induced by MPTP was observed even 14 days after the last MPTP administration, as is clear from FIG. 2 showing the results of Experiment 2, this reduction in the contents thereof was irreversible, and it is suggested that dopamine-depleted mice are extremely suitable as an animal model for Parkinson's disease.

Experiment 2

Inhibitory Effect on MPTP-induced Dopaminergic Neurodegeneration:

MPTP hydrochloride was intraperitoneally administered to C57 black male mice (11-week-old) at a dose of 30 mg/kg once a day for 8 days repetitively in the same manner as in Experiment 1. The test drugs, i.e., antiepileptic agents, were suspended in a 0.5% aqueous tragacanth solution, and the resultant was orally administered to the mice in a volume of 0.1 ml per 10 g of body weight 30 minutes prior to the MPTP administration for 8 days. Twenty-four hours, and further 14 days after the last MPTP administration in the experiment of zonisamdie and carbamazepine, the head of the mouse was subjected to microwave irradiation, and the striatum was excised therefrom. The contents of dopamine and a metabolite thereof in the striatum were measured in the same manner as in Experiment 1. In the experiments of various antiepileptic agents, zonisamide (ZNS), carbamazepine (CBZ), and the group consisting of phenytoin (PHT), lamotrigine (LTG), phenobarbital (PB), ethosuximide (ESM), sodium valproate (VPA), diazepam (DZP) and acetazolamide (AZA) were tested on the different days. The dosages for each administration of various antiepileptic agents are shown below. In addition, the values in parentheses following the dosages mean the ratio to the dose exhibiting the anticonvulsant activity in mice. As the doses exhibiting the anticonvulsant activity, the values described in Epilepsia, 27, 483 (1986) for lamotrigine and diazepam, and the values described in Arzneim. Forsch. (Drug Res.), 30, 477 (1980) for other antiepileptic agents were employed, respectively.

Zonisamide (ZNS): 10, 30, 100 mg/kg (about 0.5-fold, about 1.5-fold, about 5.1-fold, respectively)

Carbamazepine (CBZ): 20, 60 mg/kg (about 1.5-fold, about 4.5-fold, respectively)

Phenytoin (PHT): 30 mg/kg (about 3.8-fold)

Lamotrigine (LTG): 30 mg/kg (about 11.5-fold)

Phenobarbital (PB): 40 mg/kg (about 3.4-fold)

Ethosuximide (ESM): 600 mg/kg (about 2.2-fold)

Sodium valproate (VPA): 800 mg/kg (about 2.5-fold)

Diazepam (DZP): 5 mg/kg (about 4.2-fold) and

Acetazolamide (AZA): 100 mg/kg (about 3.8-fold)

The inhibitory effect of various antiepileptic agents on dopaminergic neurodegeneration 24 hours after the last MPTP administration is shown in Table 1, from the viewpoint of the contents of dopamine and a metabolite thereof, 3,4-dihydroxyphenylacetic acid (DOPAC), in the striatum, and the inhibitory rate. The inhibitory rate was calculated from the values in the normal animal group, the vehicle-treated group and the test drug-treated group. The values in Table represent a mean value ± a standard error, and the marks * and ** mean that there is a significant difference from the value of the vehicle-treated group with $p<0.05$ and $p<0.01$, respectively.

Further, the inhibitory effect of zonisamide and carbamazepine on dopaminergic neurodegeneration 14 days after the last MPTP administration (5 to 6 animals in each group) is shown in FIG. 2. The perpendicular lines in the figures represent standard errors, and the marks * and ** mean that there is a significant difference from the value of the vehicle-treated group with $p<0.05$ and $p<0.01$, respectively.

TABLE 1

Inhibitory effect on MPTP-induced dopaminergic neurodegeneration

| Test Drug | Dosage (mg/kg, po) | Number of animals | DA (ng/g tissue) | Inhibitory Rate (%) | DOPAC (ng/g tissue) | Inhibitory Rate (%) |
|---|---|---|---|---|---|---|
| Normal animal group | — | 8 | 8598 ± 560** | — | 421 ± 19** | — |
| Vehicle-treated group | — | 8 | 2366 ± 141 | — | 136 ± 6 | — |

TABLE 1-continued

Inhibitory effect on MPTP-induced dopaminergic neurodegeneration

| Test Drug | Dosage (mg/kg, po) | Number of animals | DA (ng/g tissue) | Inhibitory Rate (%) | DOPAC (ng/g tissue) | Inhibitory Rate (%) |
|---|---|---|---|---|---|---|
| ZNS | 10 | 9 | 3797 ± 201* | 22.3 | 221 ± 11* | 29.8 |
|  | 30 | 6 | 7373 ± 685** | 80.3 | 370 ± 27** | 82.1 |
|  | 100 | 8 | 8434 ± 336** | 97.2 | 447 ± 24** | 109.1 |
| Normal animal group | — | 6 | 6558 ± 743** | — | 416 ± 56** | — |
| Vehicle-treated group | — | 5 | 1932 ± 355 | — | 138 ± 27 | — |
| CBZ | 20 | 4 | 3087 ± 453 | 25.0 | 251 ± 36 | 40.6 |
|  | 60 | 5 | 2894 ± 750 | 20.8 | 202 ± 52 | 23.0 |
| Normal animal group | — | 5 | 7485 ± 705** | — | 543 ± 22** | — |
| Vehicle-treated group | — | 5 | 2029 ± 353 | — | 133 ± 19 | — |
| PHT | 30 | 6 | 4073 ± 454* | 37.4 | 257 ± 30* | 30.2 |
| LTG | 30 | 6 | 4844 ± 676** | 51.6 | 273 ± 31** | 34.1 |
| PB | 40 | 6 | 3310 ± 544 | 23.5 | 200 ± 32 | 16.3 |
| ESM | 600 | 4 | 1008 ± 182 | -18.7 | 80 ± 10 | -12.9 |
| VPA | 800 | 4 | 2984 ± 468 | 17.5 | 187 ± 29 | 13.2 |
| DZP | 5 | 4 | 3356 ± 451 | 24.3 | 208 ± 28 | 18.3 |
| AZA | 100 | 6 | 1803 ± 428 | -4.1 | 138 ± 23 | 1.2 |

As is clear from Table 1 and FIG. 2, zonisamide (ZNS) of the present invention showed a dose-dependent inhibitory effect on the MPTP-induced reduction in the contents of dopamine (DA) and a metabolite thereof, 3,4-dihydroxyphenylacetic acid (DOPAC), in the striatum in both the 24-hours group and the 14-days group, from a dose of 10 mg/kg, which is about 0.5-fold the dose exhibiting the anticonvulsant activity. Especially, zonisamide showed an extremely high inhibitory effect on the reduction in the contents of both dopamine and DOPAC at a dose of 30 mg/kg (a dose which is about 1.5-fold the dose exhibiting the anticonvulsant activity), and showed almost 100% inhibitory rate at a dose of 100 mg/kg (a dose which is about 5.1-fold the dose exhibiting the anticonvulsant activity).

On the other hand, as is clear from Table 1 and FIG. 2, carbamazepine (CBZ) did not show any significant inhibitory effect on the MPTP-induced reduction in the contents of dopamine and DOPAC in the striatum in both the 24-hours group and the 14-days group. In addition, among the other antiepileptic agents, ones other than lamotrigine (LTG) and phenytoin (PHT) could not inhibit the reduction in the contents of dopamine and DOPAC in the striatum even at a dose which is 2-fold or more the dose exhibiting the anticonvulsant activity. Although phenytoin significantly inhibited the reduction in the contents of dopamine and DOPAC at a dose of 30 mg/kg (a dose which is about 3.8-fold the dose exhibiting the anticonvulsant activity), the inhibitory rates thereof were merely 37.4% and 30.2%, respectively. Lamotrigine inhibited the reduction in the contents of dopamine and DOPAC more strongly than phenytoin at a dose of 30 mg/kg (a dose which is about 11.5-fold the dose exhibiting the anticonvulsant activity), but the inhibitory rates thereof were merely 51.6% and 34.1%, respectively, which are much weaker than the inhibitory rates, 80.3% and 82.1%, of zonisamide at a dose of 30 mg/kg (a dose which is about 1.5-fold the dose exhibiting the anticonvulsant activity).

As is clear from the results of the above Experiments, zonisamide and alkali metal salts thereof show extremely potent inhibitory effects on the MPTP-induced dopaminergic neurodegeneration at a dose exhibiting the anticonvulsant activity with low toxicity, and hence, they can be used as a medicament for neurodegenerative diseases in the prevention and treatment of various neurodegenerative diseases such as primary or secondary Parkinson's disease, Huntington's disease, choreic syndrome and dystonic syndrome in mammals (including human). The medicament of the present invention can be administered through any of oral, parenteral and intrarectal routes. The dosage of zonisamide or alkali metal salts thereof may vary depending on the administration route, the kinds of diseases to be treated, the severity of symptoms, the age of patients, etc., but it is usually in the range of 1 to 50 mg/kg/day, preferably in the range of 2 to 20 mg/kg/day, which may be administered at a time or in several times.

Zonisamide and alkali metal salts thereof can be used as a medicament for neurodegenerative diseases alone or in the form of a pharmaceutical composition, which is prepared by mixing with a pharmaceutically acceptable carrier or diluent. The pharmaceutical composition may be in the dosage forms such as tablets, capsules, granules, powders, syrups, injection preparations, and suppositories, and can be prepared by a conventional method. In addition, tablets and powders of zonisamide which are commercially available as an antiepileptic agent may be employed as a medicament for neurodegenerative diseases of the present invention.

The pharmaceutically acceptable carrier or diluent may be any conventional ones, which are commonly used in the pharmaceutical field and do not react with zonisamide or alkali metal salts thereof. Suitable examples of the pharmaceutically acceptable carrier or diluent for the preparation of tablets, capsules, granules and powers include excipients (e.g., lactose, corn starch, sucrose, mannitol, calcium sulfate, or crystalline cellulose), disintegrators (e.g., carmellose sodium, modified starch, or carmellose calcium), binders (e.g., methylcellulose, gelatin, acacia, ethylcellulose, hydroxypropylcellulose, or polyvinylpyrrolidone), and lubricants (e.g., light anhydrous silicic acid, magnesium stearate, talc, or hydrogenated oil). The tablets may be coated in a conventional manner by using conventional coating agents such as carnauba wax, hydroxypropylmethylcellulose, macrogol, hydroxypropyl methylphthalate, cellulose acetate phthalate, sucrose, titanium oxide, sorbitan fatty acid ester, and calcium phosphate.

Suitable examples of the pharmaceutically acceptable carrier or diluent for the preparation of syrups include sweetening agents (e.g., sucrose, glucose, or fructose), suspending agents (e.g., acacia, tragacanth, carmellose sodium, methylcellulose, sodium alginate, crystalline cellulose, or veegum), and dispersing agents (e.g., sorbitan fatty acid ester, sodium lauryl sulfate, or polysorbate 80). In the preparation of syrups, a flavoring agent, a perfume or a preservative may optionally be added. Further, such syrups may be in the form of a dry syrup, which is dissolved or suspended when used.

Suitable examples of the base for suppositories include cacao butter, glycerin saturated fatty acid ester, glycerogelatin, and macrogol. In the preparation of suppositories, a surfactant or a preservative may optionally be added.

Injection preparations may be usually prepared by dissolving an alkali metal salt of zonisamide in distilled water for injection, and thereto may be optionally be added a solubilizer, a buffering agent, a pH adjusting agent, an isotonic agent, a pain-reducing agent or a preservative.

These pharmaceutical compositions may contain zonisamide or an alkali metal salt thereof as an active ingredient in an amount of at least 0.5% (% by weight, hereinafter, the same), preferably 10–70%, based on the total weight of a composition. These pharmaceutical compositions may optionally contain other therapeutically effective compounds as mentioned below.

The medicaments for neurodegenerative diseases of the present invention may be administered together with other medicaments such as dopamine replenishing agents (e.g., levodopa alone, or a combination product or combined therapy of levodopa and carbidopa), dopaminergic agonists (e.g., bromocriptine or terguride), dopamine releasing agents (e.g., amantadine), anticholinergic agents (e.g., biperiden or trihexyphenidyl), and monoamine oxidase type B (MAO-B) inhibitors (e.g., selegiline).

The pharmaceutical compositions of the medicaments for neurodegenerative diseases according to the present invention are exemplified below.

Preparation 1: Tablets:

| | |
|---|---|
| Zonisamide | 100 g |
| Lactose | 35 g |
| Corn starch | 17 g |
| Crystalline cellulose | 40 g |
| Hydroxypropylcellulose | 6 g |
| Light anhydrous silicic acid | 1 g |
| Magnesium stearate | 1 g |
| Total | 200 g |

Among the above components, zoniamide, lactose, corn starch and crystalline cellulose are blended, and thereto is added hydroxypropylcellulose being dissolved in water, and the mixture is kneaded, dried and granulated. To these granules are added magnesium stearate and light anhydrous silicic acid, and the mixture is compressed to give 1000 tablet cores weighing 200 mg each. Then, said tablet cores are coated to form film-coated tablets by a conventional method, using hydroxypropylmethylcellulose, macrogol, titanium oxide, talc and light anhydrous silicic acid.

Preparation 2: 20% Powders

| | |
|---|---|
| Zonisamide | 200 g |
| Lactose | 719 g |
| Hydroxypropylcellulose | 20 g |
| Light anydrous silicic acid | 1 g |
| Total | 940 g |

Using a high-shear granulator, the above all components are blended, sprayed with an ethanolic solution (200 g) containing ethylcellulose (40 g) and hydroxypropylcellulose (20 g) for granulation, and made into granules. These are dried and regulated in size to give 20% powders.

INDUSTRIAL APPLICABILITY

As explained above, zonisamide and alkali metal salts thereof show a potent inhibitory effect on dopaminergic neurodegeneration at a dose exhibiting the anticonvulsant activity, and hence, they are useful as a medicament for neurodegenerative diseases in the prevention and treatment of various neurodegenerative diseases such as parkinson's disease, huntington's disease, choreic syndrome and dystonic syndrome in mammals (including human).

What is claimed is:

1. A method for the prevention and/or treatment of neurodegenerative diseases in a mammal which comprises administering an effective amount of zonisamide or an alkali metal salt thereof to said mammal in need of such prevention and/or treatment.

2. The method for the prevention and/or treatment according to claim 1, wherein the neurodegenerative disease is Parkinson's disease.

3. The method for the prevention and/or treatment according to claim 1, wherein the daily dosage is in the range of 1 to 50 mg per kg of body weight of a mammal.

4. The method for the prevention and/or treatment according to claim 3, wherein the daily dosage is in the range of 2 to 20 mg per kg of body weight of a mammal.

5. The method for the prevention and/or treatment according to claim 2, wherein the daily dosage is in the range of 1 to 5 mg per kg of body weight of a mammal.

6. A The method for the prevention and/or treatment according to claim 5, wherein the daily dosage is in the range of 2 to 20 mg per kg of body weight of a mammal.

7. The method for the prevention and/or treatment according to claim 1, wherein the mammal is human.

8. The method for the prevention and/or treatment according to claim 2, wherein the mammal is human.

9. The method for the prevention and/or treatment according to claim 3, wherein the mammal is human.

10. The method for the prevention and/or treatment according to claim 4, wherein the mammal is human.

11. The method for the prevention and/or treatment according to claim 5, wherein the mammal is human.

12. The method for the prevention and/or treatment according to claim 6, wherein the mammal is human.

13. A method for the prevention and/or treatment of neurodegenerative diseases in a mammal which comprises administering an effective amount of zonisamide to said mammal in need of such prevention and/or treatment.

14. The method for the prevention and/or treatment according to claim 13, wherein the neurodegenerative disease is Parkinson's disease.

15. The method for the prevention and/or treatment according to claim 13, wherein the daily dosage is in the range of 1 to 50 mg per kg of body weight of a mammal.

16. The method for the prevention and/or treatment according to claim 15, wherein the daily dosage is in the range of 2 to 20 mg per kg of body weight of a mammal.

17. The method for the prevention and/or treatment according to claims 14, wherein the daily dosage is in the range of 1 to 50 mg per kg of body weight of a mammal.

18. The method for the prevention and/or treatment according to claim 17, wherein the daily dosage is in the range of 2 to 20 mg per kg of body weight of a mammal.

19. The method for the prevention and/or treatment according to claim 13, wherein the mammal is human.

20. The method for the prevention and/or treatment according to claim 14, wherein the mammal is human.

21. The method for the prevention and/or treatment according to claim 15, wherein the mammal is human.

22. The method for the prevention and/or treatment according to claim 16, wherein the mammal is human.

23. The method for the prevention and/or treatment according to claim 17, wherein the mammal is human.

24. The method for the prevention and/or treatment according to claim 18, wherein the mammal is human.

* * * * *